United States Patent
Haberman et al.

(10) Patent No.: US 7,338,532 B2
(45) Date of Patent: Mar. 4, 2008

(54) ALIGNMENT ASSEMBLY FOR A PROSTHESIS

(75) Inventors: Louis J Haberman, Denville, NJ (US); Laszlo E Dallos, Branchville, NJ (US)

(73) Assignee: Engineered Silicone Products L.L.C., Newton, NJ (US)

( * ) Notice: Subject to any disclaimer, the term of this patent is extended or adjusted under 35 U.S.C. 154(b) by 92 days.

(21) Appl. No.: 11/140,669

(22) Filed: May 27, 2005

(65) Prior Publication Data

US 2005/0267600 A1 Dec. 1, 2005

Related U.S. Application Data

(60) Provisional application No. 60/575,102, filed on May 27, 2004.

(51) Int. Cl.
*A61F 2/80* (2006.01)
(52) U.S. Cl. .................................................. 623/38
(58) Field of Classification Search ................... 623/38
See application file for complete search history.

(56) References Cited

U.S. PATENT DOCUMENTS

| | | | |
|---|---|---|---|
| 5,464,443 A | 11/1995 | Wilson et al. | |
| 5,549,710 A * | 8/1996 | Vera et al. | 623/38 |
| 5,800,565 A | 9/1998 | Biedermann | |
| 6,398,818 B1 | 6/2002 | Merlette et al. | |
| 6,458,163 B1 * | 10/2002 | Slemker et al. | 623/38 |
| 6,488,717 B1 | 12/2002 | McColl et al. | |
| 6,692,533 B2 | 2/2004 | Johnson et al. | |
| 6,712,860 B2 | 3/2004 | Rubie et al. | |
| 2004/0059433 A1* | 3/2004 | Slemker et al. | 623/38 |

OTHER PUBLICATIONS

Hosmer Spectrum Alignment System, dated Jun. 4, 2003 by the Internet Archive Wayback Machine, 3 pages.*
Spectrum Alignment System, pp. H127-H132.*

* cited by examiner

*Primary Examiner*—Bruce Snow
(74) *Attorney, Agent, or Firm*—Harness, Dickey & Pierce, P.L.C.

(57) ABSTRACT

An alignment assembly for a modular prosthesis. The alignment assembly includes a plurality of modular components that can be selectively connected to each other for providing selectively linear adjustability along first and second non-parallel axes, and rotational/angular adjustability about three orthogonal axes.

16 Claims, 6 Drawing Sheets

ALIGNMENT ASSEMBLY FOR A PROSTHESIS

CROSS-REFERENCE TO RELATED APPLICATIONS

This application claims the benefit of U.S. Provisional Application No. 60/575,102, filed on May 27, 2004. The disclosure of the above application is incorporated herein by reference.

INTRODUCTION

Various prosthetic devices for the lower leg are known in the art.

While significant advancements have been made in the field of lower limb prosthetics in recent years, all known devices are associated with certain limitations. In this regard, known modular prosthetic components are generally not suitable for users exceeding 220 pounds. Additionally, known modular prosthetic components do not provide sufficient adjustability to ensure proper alignment and ease of adjustment for higher weight patients. Furthermore, known devices do not suitably provide a modular alignment assembly capable of connecting all known conventional modular components.

Accordingly, a need remains in the art for a prosthetic device which overcomes the limitations associated with the prior art, including but not limited to those limitations discussed above.

SUMMARY OF THE INVENTION

The present teachings provide an alignment assembly for a modular prosthesis. The alignment assembly includes a plurality of modular components that can be selectively connected to each other for providing selectively linear adjustability along at least first and second non-parallel axes, and rotational/angular adjustability about three orthogonal axes.

In one aspect, an alignment assembly according to the present teachings can include a base having first and second dovetail slots on opposite surfaces, a plurality of slidable components, each component having a dovetail adjustably receivable in one of the first and second dovetail slots, and a locking mechanism for selectively locking anyone of the slidable components in one of the first and second dovetail slots. The dovetails slots are oriented along first and second non-parallel linear adjustability axes. The locking mechanism can include first and second locking bars defined by corresponding sidewalls of the first and second dovetail slots, and at least one set screw for forcing the corresponding sidewall to lock the slidable component.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of various aspects of the present invention is merely exemplary in nature and is in no way intended to limit the invention, its application, or uses.

The present teaching provides an alignment assembly that can be installed into a modular prosthesis and can support body weights up to 425 pounds. In other instances, the alignment assembly of the present teachings can be used for pediatric applications for which dynamic loading will be significantly less.

As described below in further detail, the modular alignment assembly can provide translation/linear adjustability in at least two directions. For example, the alignment assembly can provide adjustability in an anterior/posterior (A/P) direction and a medial/lateral direction (M/L). The M/L adjustability permits optimal alignment of a prosthetic socket or limb receptacle to a prosthetic foot and/or prosthetic knee for enhanced stability. The A/P adjustability permits appropriate weight transmission over the foot and/or prosthetic knee at heel strike, mid-stance and toe-off, thereby encouraging a smooth and comfortable gait.

Angular adjustments can be facilitated by selective use of male and female connectors and/or other adapters that can be included in the alignment assembly. Additional components can be used for other rotational adjustments. The connectors and adapters can be used selectively to mate with a variety of other pre-existing female/male modular components, such as tubular clamp adapters, prosthetic knees and feet, shock absorbers, etc. The benefits of offering angular alignment adjustments are well known in the art. Such adjustments are required to orient the prosthetic socket into a position/tilt/angle matching the amputee's naturally occurring femoral or tibial angle. Permitting rotational adjustment is required to place the foot in an appropriate orientation that matches the rotational angle (toe-out) of the sound (remaining) limb. Rotational adjustments are also required to place the prosthetic knee mechanism in an externally rotated position (with respect to the line-of-progression of amputee's ambulation). This default starting position approaches 5 degrees of external rotation. However, small alteration of this rotation is often required to eliminate certain gait deviations present when such rotation is incorrectly set.

Figure 1:
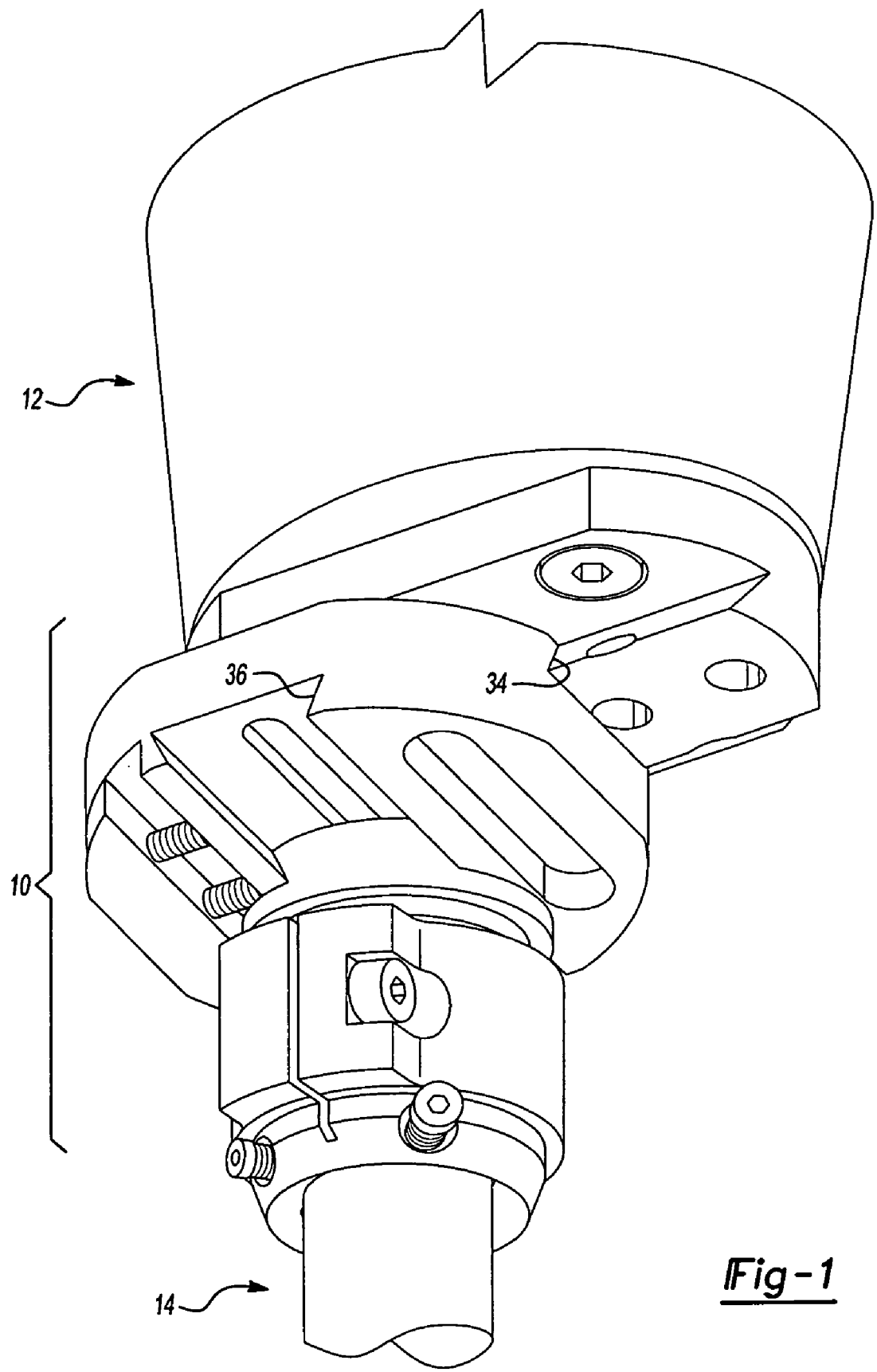
FIG. 1 is an environmental view illustrating an alignment assembly according to the present teachings, the alignment assembly incorporated into a modular lower leg prosthesis.

With initial reference to the environmental view of FIG. 1, a modular alignment assembly constructed according to the present teachings is illustrated and generally identified at reference character 10. The alignment assembly 10 is shown operably and adjustably connecting an upper prosthesis component, such as a below-knee (trans-tibial) prosthetic socket 12, and a lower prosthesis component, such as a prosthetic foot 14. The below-knee prosthetic socket 12 and the prosthetic foot 14 can be conventional components, such as those commercially available from Otto Bock Orthopedic of Duderstadt, Germany, for example.

It will be understood that the present teachings are also applicable for other applications, including, for example, an above-knee prosthesis commonly referred to as a trans-femoral prosthesis.

Referring to FIGS. 2A-2K, various exemplary components that can be used selectively and interchangeably to assemble the alignment assembly 10 of the present teachings are illustrated. The exemplary components can include a core or base 20, and various plate members, connectors, adapters and other components that can be modularly connected to the base and/or to each other. For example, the alignment assembly 10 can include an unthreaded slidable plate member 22, a threaded slidable plate member 24, a slidable male connector 26, a threadable male connector 26a, a slidable female connector 28, a threadable female connector 28a, and various other connectors. Additional components can include a rotatable housing plate 70, an unthreaded rotatable slidable adapter 72, a threaded rotatable slidable adapter 71, a slidable clamp adapter 23 having a tubular portion 19 and a clamp 13, and various other adapters. Various components of the alignment assembly 10 can be selectively assembled in various combinations depending on the particular configuration and assortment of prosthetic modular components chosen for a given prosthesis. Accordingly, the configuration and construction of the alignment assembly 10 can vary depending on the intended use environment, and may not include all the types of components illustrated.

The slidable plate members 22, 24, the slidable male connector 26, the slidable female connector 28, and the rotatable slidable adapters 72, 71, are exemplary slidable components, each of which is adapted for linear adjustability relative to the base 20. Each of these slidable components can be selectively coupled to the base 20 along a first axis A or second axis B, and linearly adjusted relative to the base 20, as described below.

Figure 2A:
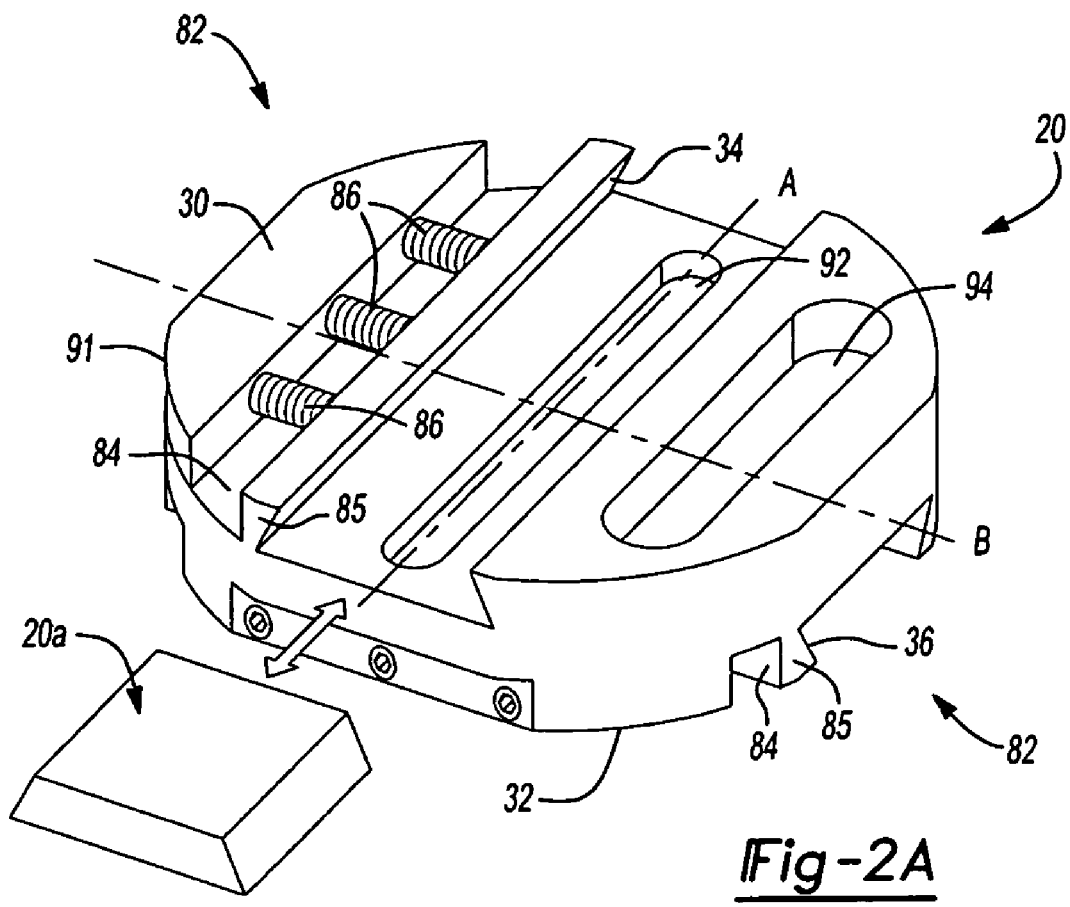
FIGS. 2A-2K are perspective views illustrating various components of the alignment assembly of the alignment assembly according to the present teachings.

With particular reference to FIG. 2A, the base 20 is further described. The base 20 can include two opposite surfaces, such as a top surface 30 and a bottom surface 32. The top and bottom surfaces 30 and 32 can have substantially identical features, which are, however, rotated through an angle, for example an angle of 90 degrees, relative to one another. Accordingly, only the features associated with the top surface 30 will be described in detail, with the understanding that identical features, but rotated 90 degrees or other angle, are associated with the bottom surface 32. In this regard, the top surface 30 can define a slot 34 which extends across the base 20 along the first axis A. The bottom surface 32 can define a slot 36 which extends across the base 20 along the second axis B. The first axis A can be perpendicular to the second axis B, or skewed at an angle other than 90 degrees, if desired. The slots 34, 36 can be, for example, dovetail slots, or other types of slots adapted for slidable attachment of various components to the base 20.

The top surface 30 of the base 20 can also define a central groove or slot 92 for engaging a corresponding fastener of a slidable component as a safety feature for preventing the slidable component from sliding completely off the base 20 while allowing slidable adjustability. Exemplary fasteners are illustrated as set screws 93 in FIGS. 2B, 2D and 2K for the plate members 22, 24, and the rotatable slidable adapter 72, respectively.

Figures 3, 4:
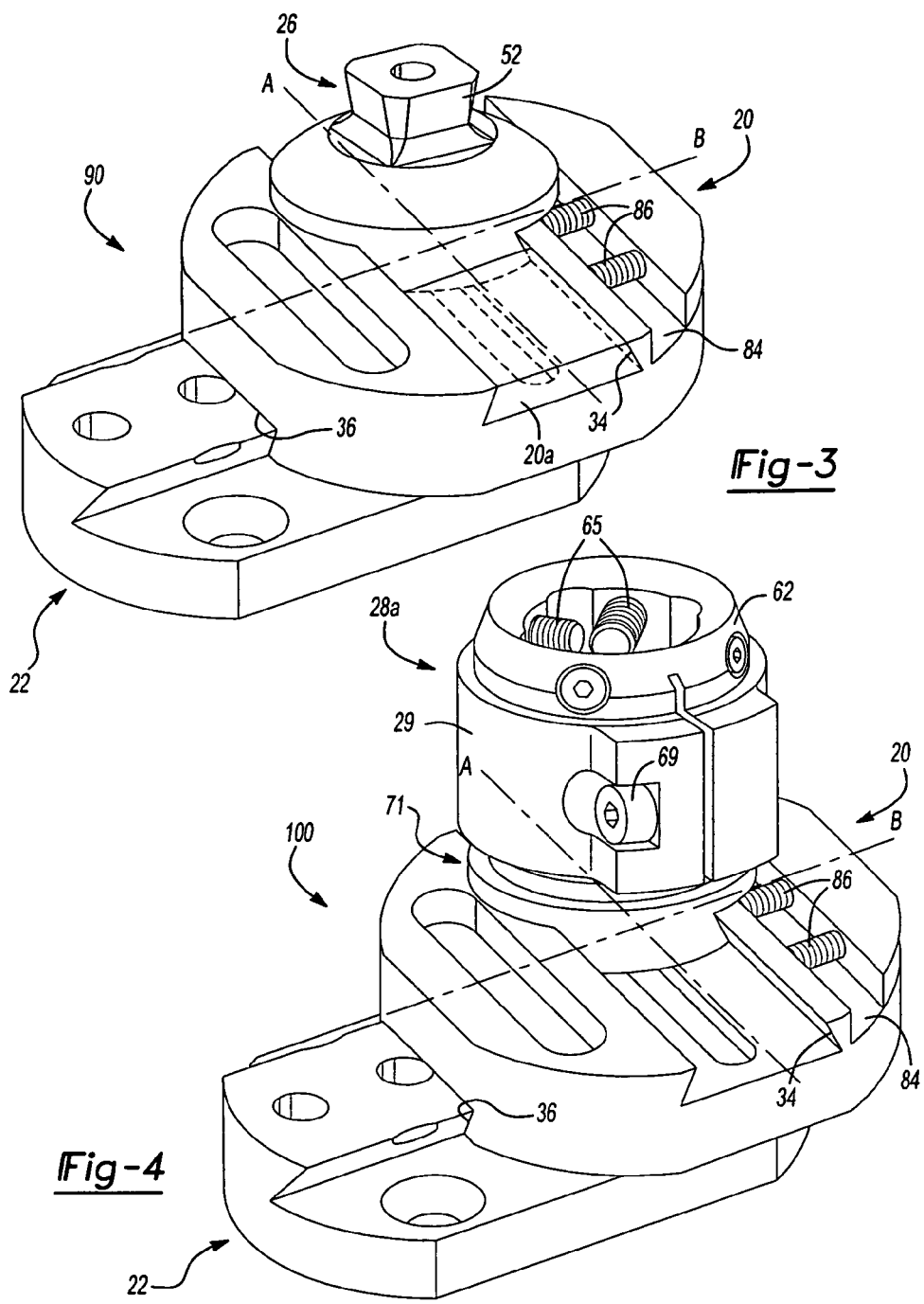
FIG. 3 is a perspective view of an exemplary construct of the alignment assembly according to the present teachings.
FIG. 4 is a perspective view of an exemplary construct of the alignment assembly according to the present teachings.

Referring to FIG. 2A, the top surface 30 of the base 20 can define a locking mechanism 82 that includes a channel 84 formed between an outer wall 91 of the base 20 and a sidewall 85 of the dovetail slot 34. The sidewall 85 functions as a locking bar that can be bent or deformed elastically by the application of appropriate transverse force. A plurality of set screws 86 can be selectively used to force the dovetail sidewall 85 into locking engagement with the slidable component for locking the slidable component in a particular position along the dovetail slot 34, as illustrated for example in FIG. 3. When a slidable component with a long dovetail that spans the entire length of the dovetail slot 34 is used, such as, for example, the dovetail 44 of the plate members 22, 24, three set screws 86 can be used for locking to prevent inadvertent sliding. The set screws 86 can be advanced against the sidewall 85 using, for example, a torque wrench or other tool that can provide the necessary torque for locking the slidable component without causing permanent deformation to the sidewall 85 or to the slidable component. A torque of 6 Nm can be applied, for example. When a slidable component that has a short dovetail, such as for example, the dovetail 50 of the slidable male connector 26, or the dovetails 76, 73 of the rotatable slidable adapters 72, 71, or the dovetail 27 of the slidable clamp adapter 23, are coupled to the base 20, a supporting slidable wedge or slider 20a can be inserted in an exposed unsupported portion of the dovetail slot 34 to prevent excessive deformation of the dovetail, as illustrated in FIG. 3. The slider 20a can be adapted to be co-operatingly received with any one of the slots 34, 36 and provide opposing forces counterbalancing the forces from the set screws 86 for preventing excessive distortions of the dovetail slot 34 caused by distortions of the sidewall 85. It will be appreciated that another locking mechanism 82 can be used on the bottom surface 32 of the base 20 in association with the second dovetail slot 36. The base 20 can also include additional grooves, slots or cutouts, such as groove 94, for example, for weight reduction.

Figure 2B:
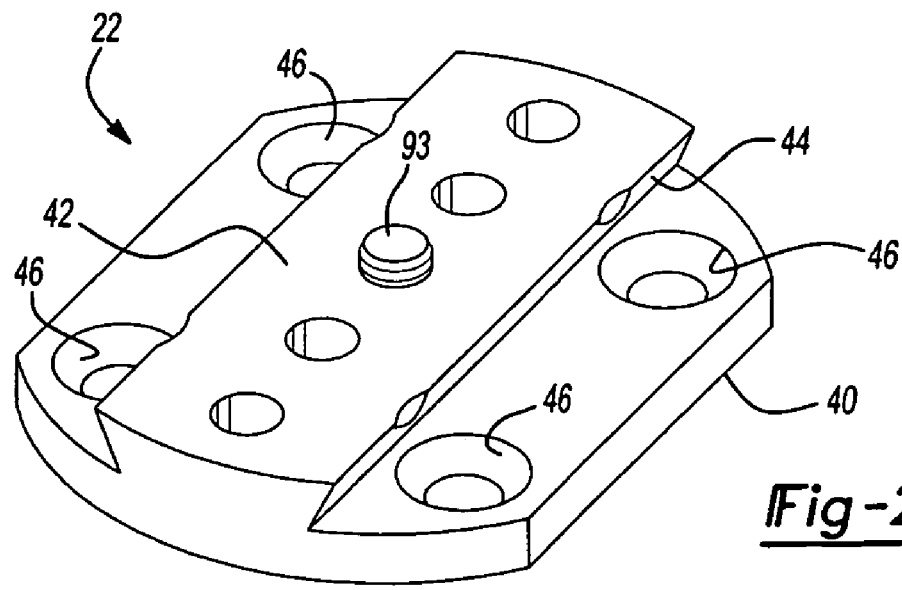
Figure 2C:
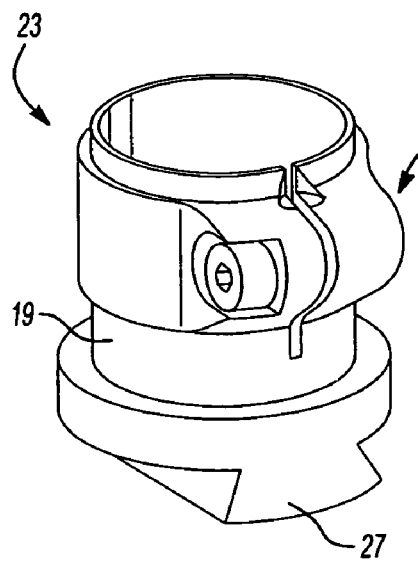
Figure 2D:
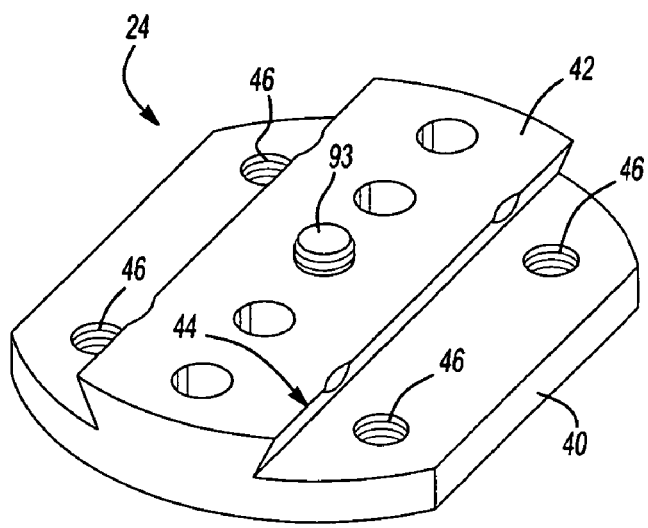

With particular reference to FIGS. 2B and 2D, the slidable plate members 22, 24 are further described. Each plate member 22, 24 can include a first generally planar side 40 and a second side 42 defining a dovetail 44. The dovetail 44 is adapted to be slidably received in one of the dovetail slots 34 or 36 of the base 20. Each plate member 22 can be conventionally attached to other components of the prosthesis with fasteners (not specifically shown). For this purpose, each plate member 22 can provided with a plurality of fastener-receiving holes 46. The holes 46 can be threaded holes as illustrated in FIG. 2D, or counterbored holes, as illustrated in FIG. 2B, depending on the intended application. Attachment plates for securing the prosthetic components to the socket 12 can be affixed to the bottom of the prosthetic socket 12. Some attachment plates are already threaded. In this instance, the counterbored plate member 22 can be used for attachment to an inner mounted socket attachment plate. Alternately, some attachment plates and/or components are not threaded, and the threaded plate member 24 can be used for attachment.

Figure 2E:
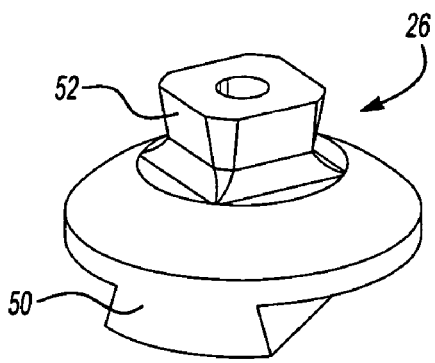
Figure 2F:
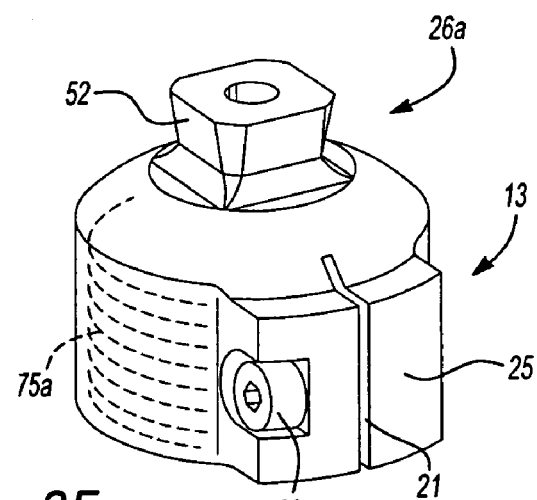

Referring particularly to FIGS. 2E and 2F, each of the exemplary male connectors 26, 26a can include a male extension 52. The male extension 52 is adapted to be attached to other components of a conventional prosthesis. As is well known in the art, the male extension 52 can have an inverted pyramidal shape or other appropriate shapes. Cooperation of the male extension 52 with one of the female connectors 28, 28a, illustrated in FIGS. 2G and 2H can provide angular adjustment, as described below.

The slidable male connector 26 can define a dovetail 50 adapted to be slidably received within one of the dovetail slots 34 or 36 of the base 20. The threadable male connector 26a can be rotatably connected to the rotatable slidable adapter 71, illustrated in FIG. 2J. The rotatable slidable adapter 71 can include an externally threaded cylindrical portion 75 that can be threaded to the interiorly threaded cylindrical portion 75a of the threadable male connector 26a. The cylindrical portion 75 of the rotatable slidable adapter 71 can include a partial slit 21 spanned by a fastener or set screw 69, forming a clamp arrangement 13. When the desired rotation is achieved, the set screw 69 can be tightened with a torque wrench to couple the threadable male connector 26a to the threaded rotatable slidable adapter 71. Similar clamp arrangements 13 can also be included in the components illustrated in FIGS. 2C, 2F and 2H. The rotatable slidable adapter 71 can also include a dovetail 73 adapted to be slidably received within one of the dovetail slots 34 or 36 of the base 20.

Each female connector 28, 28a can include a female extension 62. The female extension 62 is adapted to be attached to other components of a conventional prosthesis. The female extension 62 defines a socket 63 for rotationally receiving the male extension 52 of a component having an inverted pyramid shape, such as the male extensions 52 of the male connectors 26, 26a, or male extensions of other prosthetic components. The female extension 62 can be provided with four set screws 65 that extend into the socket 63 for engaging the male extension 52. The set screws 65 can be arranged in first and second opposing pairs, such that when the first pair of set screws 65 extends along a first direction the second pair extends at 90 degrees relative to the first pair along a second direction. This type of connection provides adjustability of rotation about any axis, because it provides rotational adjustability about three orthogonal axes, such as, for example axes $R_1$, $R_2$ and $R_3$. Rotational adjustability about axes $R_2$, $R_3$ perpendicular to axis $R_1$ is conventionally referred to as angular adjustability or tilting.

Loosening and tightening of either pair of set screws 65 can tilt the male extension 52 and the components attached above or below the male extension 52 towards the screw 65 being tightened. For example, to change an angle, one screw 65 in the medial/lateral direction is loosened and the other screw 65 media/lateral direction is tightened an equal amount. This action will cause one screw 65 to be placed deeper in its threaded hole than the opposing screw 65. The deeper screw 65 will engage the male extension 52 and tilt it in its direction.

Figure 2G:
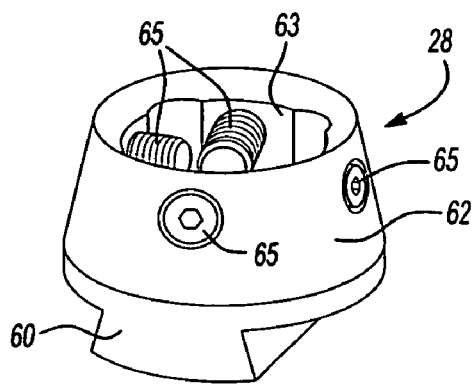
Figure 2H:
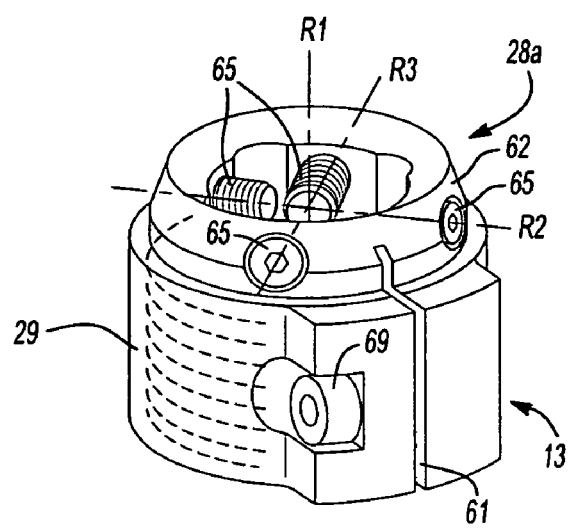
Figure 2I:
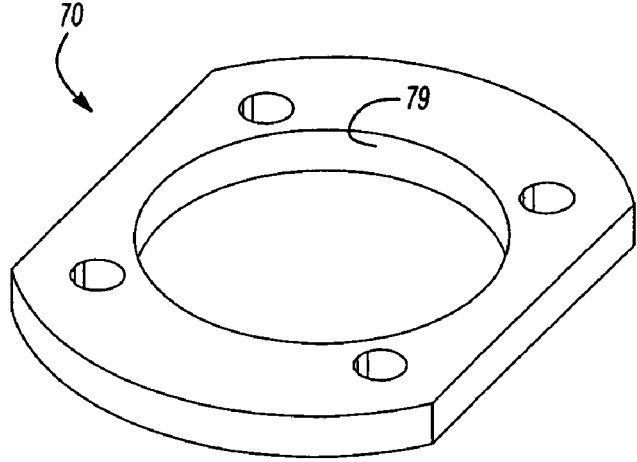
Figure 2J:
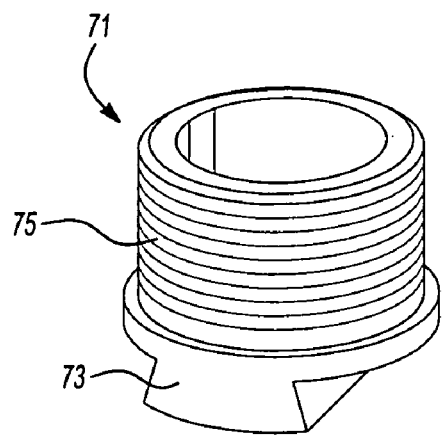
Figure 2K:
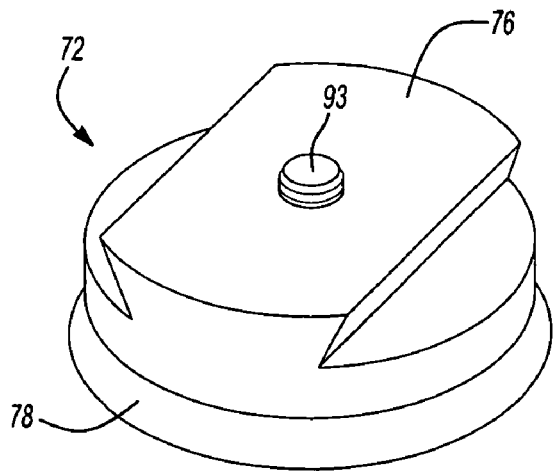

Referring to FIG. 2G, the slidable female connector 28 defines a dovetail 60 adapted to be slidably received within one of the dovetail slots 34 or 36 of the base 20. Referring to FIG. 2H, the threadable female connector 28a includes an internally threaded cylindrical portion 29 that can be threadably rotatably coupled with the threaded rotatable slidable adapter 71. The cylindrical portion 29 includes a partial slit 61 spanned by a fastener or set screw 69. When the desired rotation is achieved, the set screw 69 can be tightened with a torque wrench to secure the female connector 28a on the threaded rotatable slidable adapter 71. A torque of 9 Nm can be applied, for example.

Figure 5:
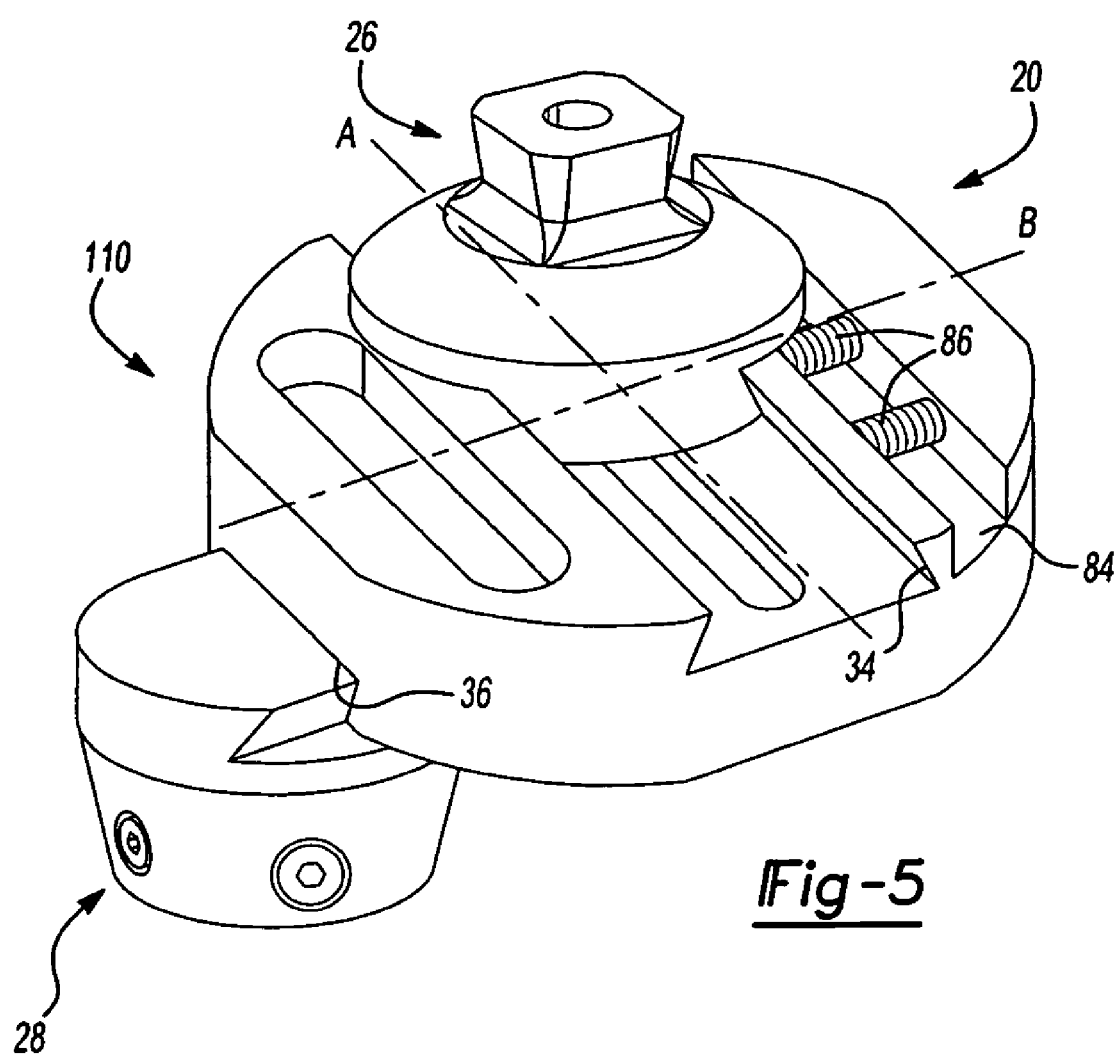
FIG. 5 is a perspective view of an exemplary construct of the alignment assembly according to the present teachings.

Referring to FIGS. 3, 4 and 5, exemplary constructs 90, 100, 110, of some of the components of the alignment assembly 10 are illustrated according to the present teachings. The construct 90 of FIG. 3 is illustrated to incorporate the base 20, the slidable plate member 22 and the slidable male connector 26. The slidable male connector 26 is coupled for linear adjustability in the direction of the first axis A relative to the base 20. The plate member 22 is coupled for linear adjustability in the direction of the second axis B relative to the base 20. The first and second axes A and B can be aligned to provide linear adjustability in two orthogonal directions, such as medial/lateral adjustment and anterior/posterior adjustment. The male extension 52 of the slidable male connector 26 can provide rotational/angular adjustability of the construct 90 when connected to a female connector 28, 28a or other female component that can receive the male extension 52, as discussed above. It will be appreciated that the construct 90 can be easily reconfigured to another construct by replacing some of the components. For example, the slidable male connector 26 can be replaced by another slidable plate member 22, 24, when angular adjustment is not required. The slidable male connector 26 can be also replaced by other slidable components, such as, for example the rotatable slidable adapter 72. The rotatable slidable adapter 72 includes a dovetail 76 which can be coupled with the dovetail slot 34 of the base 20 in the construct 90. The rotatable slidable adapter 72 also includes a cylindrical portion 78 which can be rotationally received in an opening 79 of the rotatable housing plate 70 for rotatable attachment to a prosthetic component.

Referring to FIG. 4, the exemplary construct 100 can include the base 20, the threaded rotatable slidable adapter 71, the threadable female connector 28a, and the counterbored slidable plate member 22. The slidable plate member 24 can be linearly adjusted relative to the base 20 along the second axis B. The threaded rotatable slidable adapter 71 can be linearly adjusted relative to the base 20 along the first axis A. The threadable female connector 28a can be threadably coupled to the threaded rotatable slidable adapter 71 and provide rotatable adjustability, as described above. It will be appreciated that the threaded portions 29, 75 of the female connector 28a and the threaded rotatable slidable adapter 71 can include an adequate number of threads for providing adequate rotational adjustability and a secure connection. The female connector 28a can also provide at its female extension 62 a connection to components such as the male connectors 26, 26a that include a male extension 52, for angular adjustability, as described above. Adjustability along the first axis A can provide anterior/posterior adjustment and adjustability along the second axis B can provide medial/lateral adjustment, for example.

Referring to FIG. 5, the exemplary construct 110 can include the base 20, the slidable male connector 26, and the slidable female connector 28. The slidable male connector 26 provides linear adjustability along the first axis A, and the slidable female connector 28 provides linear adjustability along the second axis B. Further, each of the male and female connectors 26, 28 can provide rotational and angular adjustability by coupling with corresponding female and male components, respectively, as discussed above.

In use, the user selects desired components of the alignment assembly 10 for coupling a given trans-tibial or trans-femoral prosthetic socket 12, and a prosthetic knee and prosthetic foot 14, as illustrated in FIG. 1. Set screws in the base 20 can be used to secure the other components once optimum alignment is achieved.

It will now be appreciated that the alignment assembly 10 of the present teachings can provide complete three-dimensional adjustability, including translational and rotational/angular adjustability about any axis. For example, the alignment assembly 10 can provide translational or linear adjustment at least in two perpendicular directions. In this regard, the alignment assembly 10 can provide adjustability in the anterior/posterior (A/P) direction and the medial/lateral direction (M/L), as discussed above. Angular adjustments can be facilitated by the use of the male or female connectors 26, 26a and 28, 28a. Rotational adjustments can be facilitated by the use of various adapters, such as, for example, adapters 71, 72, 23, illustrated in FIGS. 2J, 2K, and 2C.

The alignment assembly 10 of the present invention may be installed in virtually all new prostheses or retro-fitted into existing endoskeletal (modular) prostheses.

In one particular application, the various components of the alignment assembly 10 can be constructed of titanium, such as, for example grade 5 titanium. Those skilled in the art, however, will appreciate that other materials having suitable strength and durability characteristics may be used within the scope of the present teachings.

The dovetail connections between the components of the alignment assembly 10 enables the alignment assembly 10 to accommodate heavier loads as compared to known constructions because to its titanium construction, larger dovetails and dovetail slots and thicker base 20. In this regard, loads can be safely transferred through the alignment assembly 10 from heel strike to toe-off. Loads up to 425 pounds, for example, can be accommodated.

Throughout the drawings, the base 20 is shown to define a pair of dovetail slots 34, 36 for receiving conforming dovetails of slidable components. It will be readily appreciated that the base 20 can be alternatively be formed to include dovetails and the cooperating slidable components formed to include conforming dovetail slots. Such a variation will be understood to fall clearly within the scope of the present teachings.

As described herein, linear adjustment can be manually accomplished using the locking mechanism 82. An alternative locking mechanism can include set screws threaded through the base 20 for engaging the slidable components directly without bending of an intervening locking bar/sidewall 85. Alternatively, a worm gear (not shown) can be incorporated into the alignment assembly 10 to provide driven adjustability between the base 20 and the various cooperating slidable components. In this regard, the base 20 can be alternatively constructed to include a worm gear disposed parallel to one or both of the axes A and B. The worm gear can threadably engage a rack carried by the cooperating slidable component. In such an arrangement, the need to loosen and tighten set screws for locking can be eliminated. Rather, the threaded engagement between the worm gear and the rack can maintain a desired orientation between the components.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An alignment assembly for a modular orthopedic prosthesis, the alignment assembly comprising:
   a substantially planar base component connectable to a first prosthetic component, the base component defining first and second external dovetail recesses and first and second externally open channels on opposite first and second outer surfaces of the base component, the first dovetail recess oriented along a first axis and having a first recess length, the second dovetail recess oriented along a second axis nonparallel relative to the fist axis and having a second recess length, the first channel substantially parallel to the first dovetail recess and separated from the first dovetail recess by a first deformable locking bar, the second channel substantially parallel to the second dovetail recess and separated from the second dovetail recess by a second deformable locking bar;
   a connecting first component slidably couplable with the base component, the first component having a dovetail projection with a solid dovetail cross-section extending from a first outer surface of the first component, the dovetail projection slidably receivable in and mateable to one of the first and second dovetail recesses of the base, the dovetail projection having a length that is less than any one of the first or second recess lengths, such that when the first component is coupled to the base component, a first portion of the corresponding dovetail recess is engaged with the dovetail projection and a remaining portion of the corresponding dovetail recess is open;
   a substantially planar slider plate having a solid dovetail cross-section, the slider plate slidably receivable in and mateable to any one of the first or second of the dovetail recesses and having length substantially equal to the remaining portion of the corresponding recess when the first component is coupled to the base, the slider plate operable to stabilize the remaining portion of the recess; and
   at least one set screw transversely insertable through one of the first or second channels and operable to deform the corresponding locking bar and lock the first component to the base component.

2. The alignment assembly of claim 1, further comprising a fastener threadable though a hole of the dovetail projection of the first component perpendicularly to the base component, the fastener engageable to a longitudinal groove of the first dovetail recess for limiting relative sliding between the first component and the base component.

3. The alignment assembly of claim 1, wherein at least the base component is made of titanium.

4. The alignment assembly of claim 1, wherein the first axis is perpendicular to the second axis.

5. The alignment assembly of claim 1, in combination with an upper prosthetic component and a lower prosthetic component.

6. The alignment assembly of claim 5, wherein the assembly can support body weights up to 425 pounds.

7. The alignment assembly of claim 5, further comprising a second component, wherein the first component is coupled to the upper prosthetic component and the second component is coupled to the base component and to the lower prosthetic component.

8. The alignment assembly of claim 7, wherein one of the first and second components defines a generally planar surface for engaging one of the upper and lower prosthetic components.

9. The alignment assembly of claim 7, wherein one of the first and second components defines a male extension for engaging one of the upper and lower prosthetic components.

10. The alignment assembly of claim 7, wherein one of the first and second components defines a female extension for receiving one of the upper and lower prosthetic components.

11. The alignment assembly of claim 1, wherein the first component further comprises a female connector couplable with another component for rotational adjustability about at least two orthogonal axes.

12. The alignment assembly of claim 1, wherein the first component further comprises a male connector couplable with another component for rotational adjustability about at least two orthogonal axes.

13. An alignment assembly for a modular orthopedic prosthesis, the alignment assembly comprising:

a substantially planar base component connectable to a first prosthetic component, the base component defining first and second external dovetail recesses and first and second externally open channels on opposite first and second outer surfaces of the base component, the first dovetail recess oriented along a first axis, the second dovetail recess oriented along a second axis nonparallel relative to the fist axis, the first channel substantially parallel to the first dovetail recess and separated from the first dovetail recess by a first deformable locking bar, the second channel substantially parallel to the second dovetail recess and separated from the second dovetail recess by a second deformable locking bar, at least one of the dovetail recesses defining a central longitudinal groove;

a plurality of connecting components slidably couplable with the base component, each connecting component having a dovetail projection extending from a first outer surface of the connecting component, the projection having a solid cross-section that closely conforms in shape to each of the first and second dovetail recesses, the projection slidably receivable in and mateable to one of the first and second dovetail recesses of the base component; and a fastener threadable through a through-hole of the dovetail projection of one of the plurality of connecting components, the fastener perpendicular to the base component and engageable to the longitudinal groove.

14. The alignment assembly of claim 13, further comprising at least one set screw transversely insertable through one of the first or second channels of the base component and operable to deform the corresponding locking bar for locking one of the connecting components to the base component.

15. The alignment assembly of claim 13, further comprising a substantially planar slider plate having a solid dovetail cross-section, the slider plate slidably receivable in and mateable to the first dovetail recess along a remaining portion of the first dovetail recess when one of the plurality of the connecting components is slidably engaged to another portion of first recess, the slider plate operable to stabilize the remaining portion of the recess.

16. The alignment assembly of claim 13, wherein at least the base component is made of titanium.

* * * * *